(12) United States Patent
Lin et al.

(10) Patent No.: US 10,493,105 B2
(45) Date of Patent: Dec. 3, 2019

(54) ISOLATED ADIPOSE-DERIVED MESENCHYMAL STEM CELLS TREATED WITH ANGELICA EXTRACT OR BUTYLIDENEPHTHALIDE, AND WHEREIN THE CELLS HAVE AN INCREASED MITOCHONDRIAL MEMBRANE POTENTIAL AND A DECREASED LEVEL OF IL-8, AND METHODS FOR TREATING PARKINSON'S DISEASE

(71) Applicant: Taiwan Mitochondrion Applied Technology Co., Ltd, Zhubei, Hsinchu County (TW)

(72) Inventors: Shinn-Zong Lin, Taichung (TW); Horng-Jyh Harn, Taichung (TW); Shih-Ping Liu, Taichung (TW); Han-Chung Cheng, Zhubei (TW); Chi-Tang Tu, Zhubei (TW)

(73) Assignee: TAIWAN MITOCHONDRION APPLIED TECHNOLOGY CO., LTD, Zhubei, Hsinchu County (TW)

( * ) Notice: Subject to any disclaimer, the term of this patent is extended or adjusted under 35 U.S.C. 154(b) by 0 days.

(21) Appl. No.: 15/857,270

(22) Filed: Dec. 28, 2017

(65) Prior Publication Data
US 2018/0117090 A1     May 3, 2018

Related U.S. Application Data

(63) Continuation-in-part of application No. 14/851,402, filed on Sep. 11, 2015, now abandoned.
(Continued)

(51) Int. Cl.

| | |
|---|---|
| *C12N 5/07* | (2010.01) |
| *C12N 5/071* | (2010.01) |
| *C12N 5/079* | (2010.01) |
| *C12N 5/0793* | (2010.01) |
| *C12N 5/0797* | (2010.01) |
| *C12N 5/0735* | (2010.01) |
| *C12N 5/074* | (2010.01) |
| *C12N 5/077* | (2010.01) |
| *C12N 5/0775* | (2010.01) |
| *C12N 5/0789* | (2010.01) |
| *G01N 33/567* | (2006.01) |
| *A01N 1/00* | (2006.01) |
| *A61K 48/00* | (2006.01) |
| *A01N 63/00* | (2006.01) |
| *A61K 35/28* | (2015.01) |
| *C07K 14/575* | (2006.01) |
| *A61K 9/00* | (2006.01) |
| *A61P 25/16* | (2006.01) |
| *A61K 38/18* | (2006.01) |
| *A01K 67/027* | (2006.01) |

(Continued)

(52) U.S. Cl.
CPC ............ *A61K 35/28* (2013.01); *A01K 67/027* (2013.01); *A61K 9/0019* (2013.01); *A61K 9/0085* (2013.01); *A61K 38/185* (2013.01); *A61P 25/16* (2018.01); *C07K 14/575* (2013.01); *C12N 5/0667* (2013.01); *A61K 35/35* (2013.01); *A61K 35/50* (2013.01); *A61K 36/232* (2013.01); *C12N 2500/16* (2013.01); *C12N 2500/30* (2013.01); *C12N 2500/38* (2013.01); *C12N 2500/76* (2013.01); *C12N 2501/11* (2013.01); *C12N 2501/999* (2013.01); *C12N 2506/13* (2013.01); *C12N 2506/1369* (2013.01)

(58) Field of Classification Search
CPC ............ C12N 2502/30; C12N 2503/02; C12N 5/0018; C12N 5/0606; C12N 5/0667; C12N 2506/1369; C12N 2500/30; C12N 2502/137; C12N 2506/13; C12N 5/064; C12N 5/0665; C12N 5/00; C12N 5/0031; C12N 5/0069; C12N 5/2501; C12N 5/2308; C12N 5/00653; C12N 5/0668; C12N 5/0662; C12N 6/0069; A61K 38/00; A61K 45/06; A61K 35/00; A61K 35/12; A61K 35/28; A61K 9/0085; A61K 35/35; A61K 35/51; A61K 35/545; A61K 35/185; A61K 2300/00; A61K 35/50; G01N 2510/00; G01N 38/6896; G01N 2333/70589; G01N 33/5005; G01N 33/4833; A61P 25/00; A61P 25/16; A61P 9/10; C12Q 2600/158

See application file for complete search history.

(56) References Cited

U.S. PATENT DOCUMENTS 9,222,073 B2 * 12/2015 Paek .................... C12Q 1/6883
9,526,679 B2    12/2016 Jang
(Continued)

FOREIGN PATENT DOCUMENTS

| CN | 107137341 | * | 9/2017 |
| EP | 2974723 | * | 1/2016 |
| WO | WO2014139318 | * | 9/2014 |

OTHER PUBLICATIONS

Liu et al. pLOS One 7:e44024. doc:101371/journal.pone.0044024. Sep 7, 20112.*
(Continued)

*Primary Examiner* — Chang-Yu Wang
(74) *Attorney, Agent, or Firm* — Muncy, Geissler, Olds & Lowe, P.C.

(57) ABSTRACT

A cell for treating neurodegenerative disease treated with *angelica* extract is provided. The pharmaceutical composition comprises the cell for treating neurodegenerative disease and can significantly increase and recover the number of dopaminergic neurons to achieve the goal for treating neurodegenerative disease.

10 Claims, 12 Drawing Sheets

Related U.S. Application Data (60) Provisional application No. 62/049,090, filed on Sep. 11, 2014.

(51) Int. Cl.
*A61K 35/50* (2015.01)
*A61K 35/35* (2015.01)
*A61K 36/232* (2006.01)

(56) References Cited

U.S. PATENT DOCUMENTS

| | | | |
|---|---|---|---|
| 9,856,454 B2* | 1/2018 | Sun | A61K 35/35 |
| 9,938,501 B2* | 4/2018 | Katz | A61K 9/0019 |
| 2006/0057657 A1 | 3/2006 | Baetscher et al. | |
| 2012/0027860 A1* | 2/2012 | Katz | A61K 9/0019 424/489 |
| 2012/0156230 A1* | 6/2012 | Abbot | A61K 35/50 424/184.1 |
| 2014/0127171 A1* | 5/2014 | Nocera | A61K 35/50 424/93.7 |
| 2014/0212970 A1 | 7/2014 | Liu et al. | |
| 2014/0271568 A1 | 9/2014 | Lin et al. | |
| 2015/0004146 A1* | 1/2015 | Peled | A61K 35/28 424/93.7 |
| 2015/0056702 A1 | 2/2015 | Liu et al. | |
| 2015/0064273 A1* | 3/2015 | Peled | A61K 35/28 424/574 |
| 2016/0184366 A1* | 6/2016 | Kerkis | A61K 35/28 424/93.7 |
| 2016/0324826 A1 | 11/2016 | Lin et al. | |
| 2018/0223258 A1* | 8/2018 | Katz | A61K 9/0019 |

OTHER PUBLICATIONS

Tsai et al. J. Neurochem. 2006; 99:1251-1262.*
Lv et al. Stem cell; 2014; 32:1408-1419.*
Joyce et al. Regen. Med. 2010; 5:93-3946.*
Frese et al. Transfus Med. Hemother. 2016; 43:268-274.*
Constantin et al. Stem cells 2009; 27:2624-2635.*
CN107137341—English translated version, published Sep. 2017.*
Choi et al. Neurobiol. Aging 2015; 36:2885-2892.*
Castorina et al. Neural Regen. Res. 2015; 10:850-858.*
Orbay et al. Stem Cells Inernational, 2012; doi:10.1155/2012/461718.*
Anwer et al. Lasers Surg. Med. 2012; 44:769-778.*
Lee et al. J. Mol. Cell. Cardiol. 2017; 104:17-30.*
Zorova et al., Anal. Biochem. 2018; 552:50-59.*
Chi et al. Cell Transplantation, 2018; 27:456-470.*
Zhang et al., PLoS One, 2013, 8(10):e77077. doi:10.1371/journal.pone.0077077.*
Fuchs et al., "Stem Cells: A New Lease on Life," Cell, vol. 100, pp. 143-155, Jan. 7, 2000.

* cited by examiner

ISOLATED ADIPOSE-DERIVED MESENCHYMAL STEM CELLS TREATED WITH ANGELICA EXTRACT OR BUTYLIDENEPHTHALIDE, AND WHEREIN THE CELLS HAVE AN INCREASED MITOCHONDRIAL MEMBRANE POTENTIAL AND A DECREASED LEVEL OF IL-8, AND METHODS FOR TREATING PARKINSON'S DISEASE

CROSS-REFERENCE TO RELATED APPLICATIONS

This Non-provisional application claims priority under 35 U.S.C. § 119(a) on Patent Application No. 62/049,030 filed in United States America [Sep. 11, 2014], the entire contents of which are hereby incorporated by reference. This application is a continuation-in-part of U.S. patent application Ser. No. 14/851,402, now abandoned, entitled "PHARMACEUTICAL COMPOSITIONS FOR TREATING DEGENERATIVE NEUROLOGICAL DISEASE WITH MITOCELLS", filed on Sep. 11, 2015, wherein the contents of which are incorporated herein by reference in their entirety.

BACKGROUND OF THE INVENTION

1. Field of the Invention

The present invention relates to a pharmaceutical composition, and particularly relates to a pharmaceutical composition for treating neurodegenerative disease, increasing the generation of dopaminergic neurons, and repairing damaged dopaminergic neurons.

2. Description of the Prior Art

Because of advances in economic development and health care, the average age of the population is increasing by the numbers of older people. Population aging has occurred as a trend. According to the report of United Nations, the world population in 2012 is about 7.08 and the population over 65 years in worldwide is 7.9% of the total population in 2012. This is an aging society defined by World Health Organization (WHO). As the world population is ageing, and the patient numbers of neurodegenerative diseases are rapidly increased, more than 400 worldwide people suffer neurodegenerative diseases. However, the neurodegenerative disease not only occurs in the elderly, but about 50% people suffer the neurodegenerative disease before age The other 50% people suffer the neurodegenerative disease after age 60. Neurodegenerative disease is a disorder condition of progressive degeneration in brain or spinal neurons, which from the destruction or loss of the synapse and myelin sheath. The disorder leads to function disturbance, walking difficulties, and death.

Parkinson's disease is more common in older people, and the most of the cases occur after the age of 50 to 79. It is characterized by the death of dopaminergic neurons in the substantia nigra. Substantia nigra has about 200,000 dopaminergic neurons in of normal human tissues. Dopaminergic neurons secrete the neurotransmitter dopamine and play important roles in neurological functions including coordinated motion control. If the degeneration is not serious, it will not cause uncoordinated movements. However, when more than 50% neurons in human are degenerated, mild symptoms may occur in the patients including shaking, rigidity, slowness of movement and difficulty with walking and gait. Later, thinking and behavioral problems may arise, with dementia commonly occurring in the advanced stages of the disease. Finally, the patients may die from respiratory tract infection, urinary tract infection, or bedsore.

Currently, the treatment of Parkinson's disease in the early stage is typically with the medications L-DOPA to increase dopamine concentrations to maintain normal dopamine concentration in blood. For early Parkinson's disease, using L-DOPA medicine can make good treatment. But the disease progresses and dopaminergic neurons are continuing lost, these drugs eventually need to take more and more, but the symptoms get more serious. Finally, the drugs become ineffective. Most people who use these medicines for many years may cause the adverse side effects including hallucinations, nausea, gastrointestinal upset, and involuntary dancing movements. Since the drugs are unable to control the symptoms in the late stage of treatment, surgery will be used to improve the quality of the life. Surgery for Parkinson's disease can be divided into three main groups: (1) Cautery incision. Target areas for lesions include the globus pallidus, thalamus, and hypothalamus nucleus. These areas are heated with 80° C. about 80 seconds to inactive the function of neuron cells; (2) Implantation of electrodes, which is similar to (1). Electrodes are inserted into the brain to reduce physical shaking; and (3) stem cell therapy. Stem cells are used to supply a source of dopaminergic neurons to replace the function of those cells lost during the neurodegenerative process and improve the symptoms of Parkinson's disease.

Although it is reported that stem cells can be used to treat Parkinson's disease and relieve symptoms, the disease cannot be cured by stem cell treatment, mainly because of low survival of stem cells injected into a subject, which is caused by immune response, and few numbers of dopaminergic neurons differentiated from the injected stem cells (Cave et al, 2014). Thus, the cell treatment still cannot treat or cure the neurodegenerative disease.

SUMMARY OF THE INVENTION

In view of the above-mentioned problem, the present invention provides a cell for treating neurodegenerative diseases, which is an adipose-derived mesenchymal stem cell treated with a 5~80 µg/ml *angelica* extract for 1 to 2 days, and the cell for treating neurodegenerative diseases has a cluster of differentiation (CD) marker expression profile of $CD34^-$, $CD45^-$, $CD73^+$, $CD90^+$, and $CD105^+$.

The present invention further provides a pharmaceutical composition for treating neurodegenerative disease, comprising the cell for treating neurodegenerative diseases of the present invention and a pharmaceutically acceptable salt.

The present invention further provides a method for treating neurodegeneratives diseases in a subject, comprising administrating a therapeutically effective number of cells for treating neurodegenerative diseases to the subject, wherein the cells for treating neurodegenerative diseases are adipose-derived mesenchymal stem cells treated with a 5~80 µg/ml *angelica* extract for 1 to 2 days, and the cells for treating neurodegenerative diseases have a cluster of differentiation (CD) marker expression profile of $CD34^-$, $CD45^-$, $CD73^+$, $CD90^+$, and $CD105^+$.

DETAILED DESCRIPTION OF THE PREFERRED EMBODIMENT

The following is a detailed description provided to aid those skilled in the art in practicing the present invention. Those of ordinary skill in the art would understand that modifications or variations of the embodiments expressly described herein, which do not depart from the spirit or scope of the information contained herein, are encompassed by the present disclosure. The terminology used in the description is for describing particular embodiments only and is not intended to be limiting of the invention. The section headings used below are for organizational purposes only and are not to be construed as limiting the subject matter described.

The present disclosure is directed to cells for treating neurodegenerative diseases, which are adipose-derived mesenchymal stem cells treated with *angelica* extract. The treated adipose-derived mesenchymal stem cells secrete more neural trophic factors than untreated adipose-derived mesenchymal stem cells. After being administrated into a subject, the treated adipose-derived mesenchymal stem cells increase the differentiation of dopaminergic neurons from neural stem cells, enhance repair of damaged dopaminergic neurons, and do not increase immune response. Therefore, the treated adipose-derived mesenchymal stem cells can be used to treat neurodegenerative diseases, especially Parkinson's disease. In some embodiments, the cell for treating neurodegenerative diseases secretes brain derived neurotrophic factor (BDNF).

*Angelica* can be dried by freeze drying, spray drying, evaporation, or heat drying, etc. In the present invention, the term "*angelica*" as used herein refers to a taproot, lateral root, or fibers of *Angelica sinensis*. The *angelica* can be extracted using an agent to obtain an *angelica* extract. For example, a supercritical fluid extraction, water extraction, or organic solvent extraction method can be used. Preferably, the *angelica* extract of the present invention comprises butylidenephthalide. In some embodiments, the *angelica* extract is butylidenephthalide.

The term "stem cell" used herein refers to a cell in an undifferentiated state that has the property of self-renewal and has the developmental potential to differentiate into multiple cell types, without a specific implied meaning regarding developmental potential. The stem cell includes embryonic and adult stem cells. Natural somatic stem cells have been isolated from a wide variety of adult tissues including blood, bone marrow, brain, olfactory epithelium, skin, pancreas, skeletal muscle, and cardiac muscle. The stem cells of the invention include, but are not limited to, adipose-derived mesenchymal stem cells, neural stem cells, neural crest stem cells, mesenchymal stem cells, hematopoietic stem cells, pancreatic stem cells, hematopoietic stem cells, skin stem cells, embryonic stem cells, endothelial stem cells, liver stem cells, intestinal epithelial stem cells and germ stem cells, preferably adipose-derived mesenchymal stem cells.

The cell for treating neurodegenerative diseases of the present invention is obtained by treating an adipose-derived mesenchymal stem cell with a medium containing the *angelica* extract and/or butylidenephthalid for at least 1 hours, preferably more than 2, 3, 4, 5, 6, 7, 8, 9, 10, 15, 20, or 24 hours, more preferably, more than 1, 2, 3, 4, 5, 6, 7, 8, 9, or 10 days.

The concentration of the *angelica* extract and/or butylidenephthalid is 5~80 µg/ml, preferably 5, 10, 15, 20, 25, 30, 35, 40, 45, 50, 55, 60, 65, 70, 75, 80 µg/ml. In some embodiments, the concentration of the *angelica* extract and/or butylidenephthalid is 20 µg/ml.

It shall be noted that the cells for treating neurodegenerative diseases of the present invention still remain the properties of stem cells after treated with *angelica* extract. For example, the untreated and the treated adipose-derived mesenchymal stem cells have a cluster of differentiation (CD) marker expression profile of CD34$^-$/CD45$^-$/CD73$^+$/CD90$^+$/CD105$^+$. Additionally, after being administrated in mice, the cells for treating neurodegenerative diseases of the present invention differentiate into neurons and secrete brain derived neurotrophic factor (BDNF) to increase differentiation of dopaminergic neurons from neural stem cells nearby and increase repair of damaged dopaminergic neurons. In some embodiments, the cells for treating neurodegenerative diseases of the present invention differentiate into a dopaminergic neuron in a subject's brain.

Stem cells majorly rely on anaerobic glycolysis to gain energy and maintain their stemness, but they still have basic mitochondrial functions that provide energy conversion into oxidative phosphorylation (OXPHOS) for subsequent cell differentiation. Therefore, mitochondrial functions play an important role in differentiation of stem cells. The cells for treating neurodegenerative diseases of the present invention, which are treated with *angelica* extract, maintain their stemness, and the mitochondrial membrane potential of the cells increases, indicating that the cells have enhanced mitochondrial functions. Therefore, after being administrated into a subject, the cells for treating neurodegenerative diseases of the present invention can accelerate their own energy conversion when differentiating into neurons.

In some embodiments, the cells for treating neurodegenerative diseases of the present invention enhances balance and coordination abilities of a mouse having a neurodegenerative disease within 2 to 5 days after the cells for treating neurodegenerative diseases were administered into the mouse.

In some embodiments, the neurodegenerative disease is Parkinson's Disease.

The present invention also provides a pharmaceutical composition for treating neurodegenerative disease, comprising the cells for treating neurodegenerative diseases of the present invention and a pharmaceutically acceptable salt.

In some embodiments, the cells for treating neurodegenerative diseases of the present invention are present in an amount of 70%-99% (w/w) of the composition. The amount of the cells for treating neurodegenerative diseases of the present invention is preferably 70%, 75%, 80%, 85%, 90%, 95%, 96%, 97%, 98%, or 99% (w/w). The present invention further provides a method for treating neurodegenerative diseases in a subject, comprising administrating a therapeutically effective number of cells for treating neurodegenerative diseases to the subject, wherein the cells for treating neurodegenerative diseases are adipose-derived mesenchymal stem cells treated with a 5~80 µg/ml *angelica* extract for 1 to 2 days, and the cells for treating neurodegenerative diseases have a cluster of differentiation (CD) marker expression profile of $CD34^-$, $CD45^-$, $CD73^+$, $CD90^+$, and $CD105^+$.

The term "therapeutically effective number" used herein refers to the number of cells for treating neurodegenerative diseases of the present invention required to confer a therapeutic effect on a subject being treated. Depending on methods of administration, excipient use, and the possibility of being used in conjunction with other therapeutic therapies, one of skill in the art will recognize that the effective number will vary.

In some embodiments, the therapeutically effective number of cells for treating neurodegenerative diseases is $1 \times 10^4$ to $1 \times 10^6$ cells per mouse, which converts to $3 \times 10^7$ to $3 \times 10^9$ cells per human being.

The pharmaceutical composition of the present invention can effectively improve the quantity and quality of neurons in brain to improve the balance and coordination abilities of the subjects. The subject of the present invention includes a human or non-human animals (e.g., mouse, dog, cat, sheep, cattle, horse, or monkey, etc), preferably, human.

More importantly, the cells for treating neurodegenerative diseases of the present invention not only effectively increase the amount of dopaminergic neurons, but decrease the subject's immune response caused by the injection. The cells for treating neurodegenerative diseases are better than untreated stem cells.

The pharmaceutical composition of the present invention can be administered alone or combined with other methods or drugs of treatment of neurodegenerative disease.

As mentioned above, the cells for treating neurodegenerative diseases of the present invention can increase the amount of dopaminergic neurons in brain, particularly in substantia nigra, to treat neurodegenerative disease, such as Parkinson's disease or Alzheimer's disease. Additionally, the risk of immune rejection of the cells for treating neurodegenerative diseases of the present invention is lower than the risk of immune rejection of untreated adipose-derived mesenchymal stem cells.

Additional specific embodiments of the present invention include, but are not limited to the following:

Example 1

Culture and Pre-Treatment of the Cells for Treating Neurodegenerative Diseases of the Present Invention The cells for treating neurodegenerative diseases of the present invention were prepared by culturing adipose-derived mesenchymal stem cells in a stem cell culture medium. The stem cell culture medium comprises Keratinocyte-SFM (1×) liquid (Gibco), bovine pituitary extract (Gibco), EGF (Gibco), N-acetyl-L-cysteine (Sigma), L-ascorbic acid phosphate magnesium salt hydrate (Sigma), 10% bovine Serum (HyClone), and 0, 5, 10, 20, 40, 80, 160, or 320 µg/µl *angelica* extract, respectively. The *angelica* extract is butylidenephthalide. The following term "the cells for treating neurodegenerative diseases" is defined as the adipose-derived mesenchymal stem cells treated with *angelica* extract.

Figure 1A:
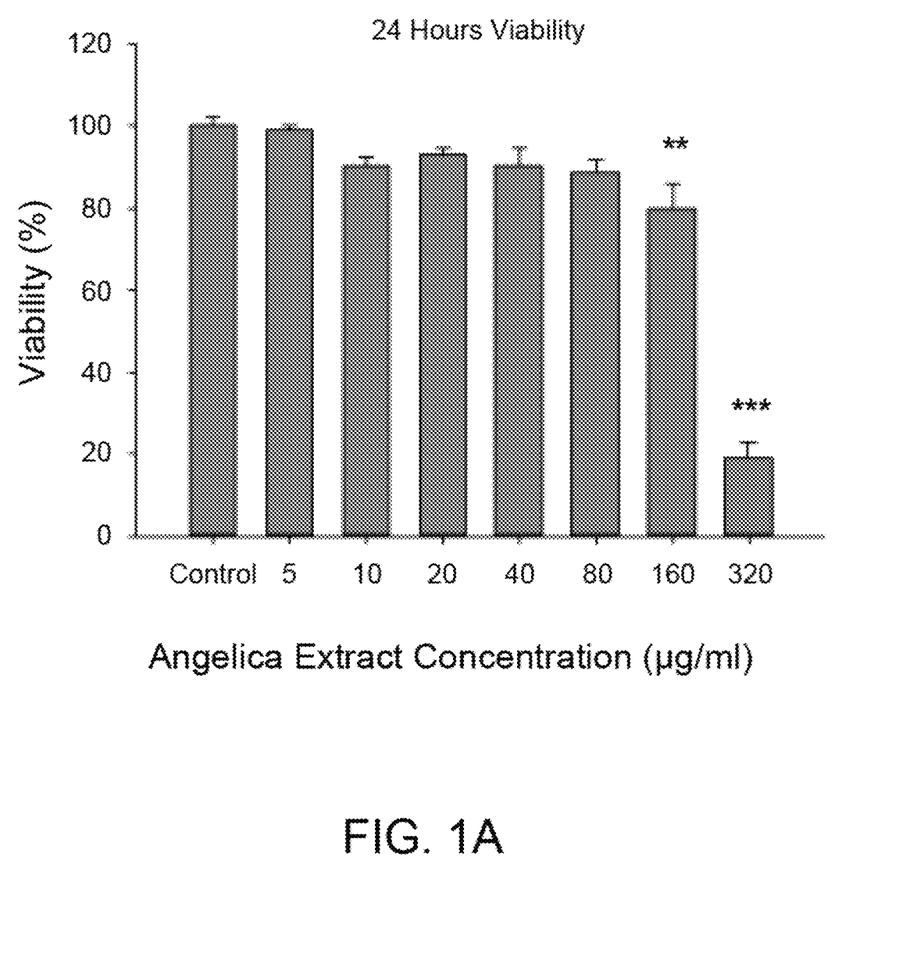
FIG. 1A illustrates the survival rate of the adipose-derived mesenchymal stem cells treated with various concentrations of *angelica* extract for 24 hours.
Figure 1B:
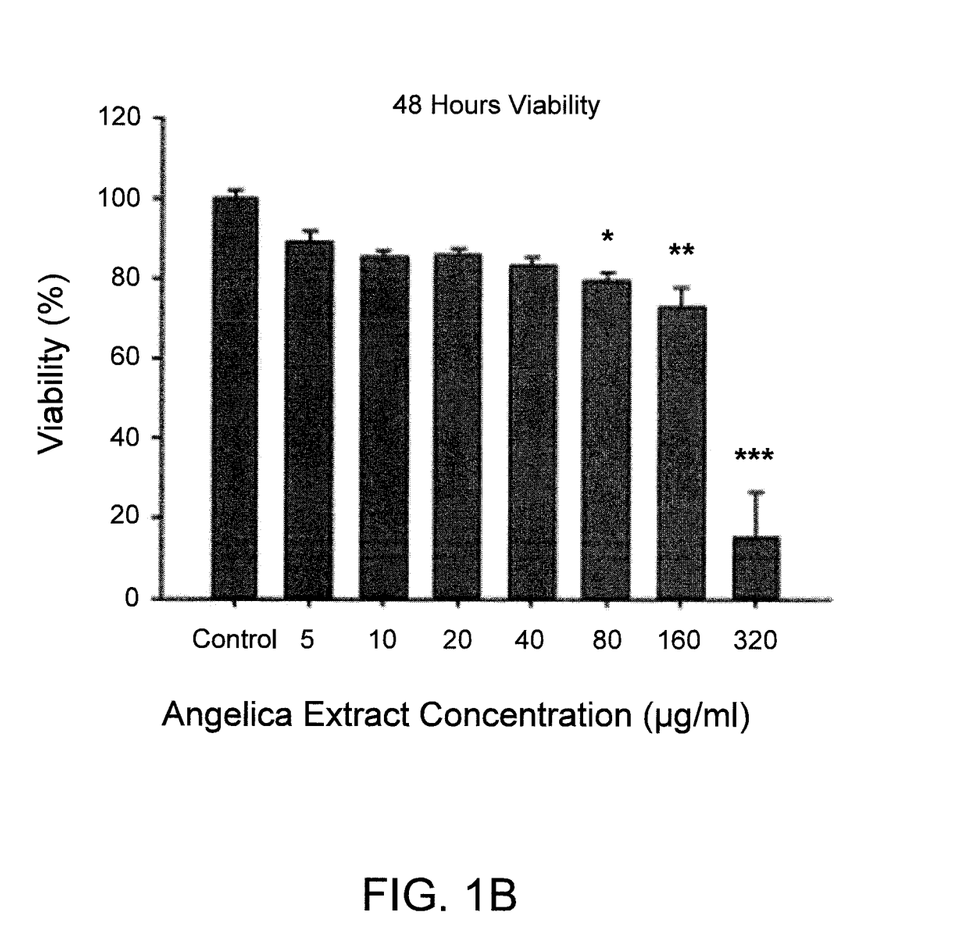
FIG. 1B illustrates the survival rate of the adipose-derived mesenchymal stem cells treated with various concentrations of *angelica* extract for 48 hours.
Figure 2A:
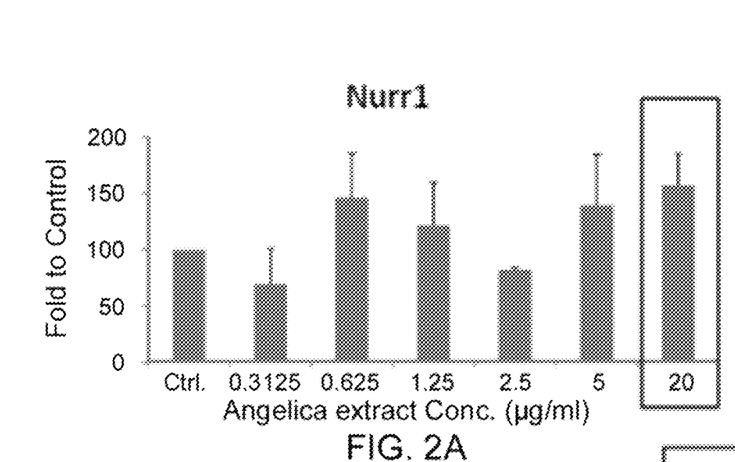
FIGS. 2A-2D show gene expressions of nuclear receptor related 1 protein (Nurr1) (FIG. 2A), brain derived neurotrophic factor (BDNF) (FIG. 2B), stromal cell-derived factor 1 (SDF1) (FIG. 2C), and Interleukin 8 (IL-8) (FIG. 2D) of the adipose-derived mesenchymal stem cells treated with various concentrations of *angelica* extract.
Figure 2B:
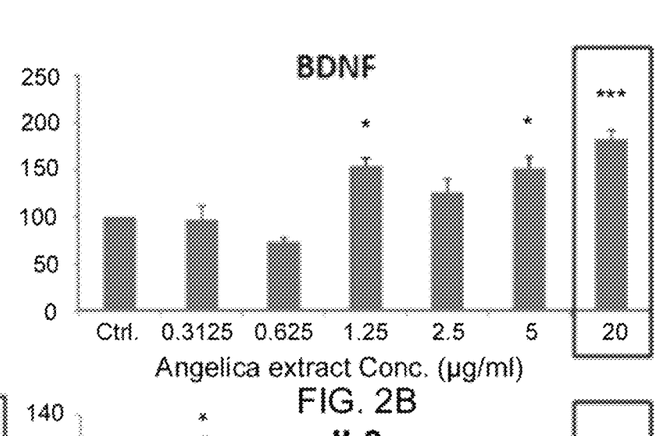
Figure 2C:
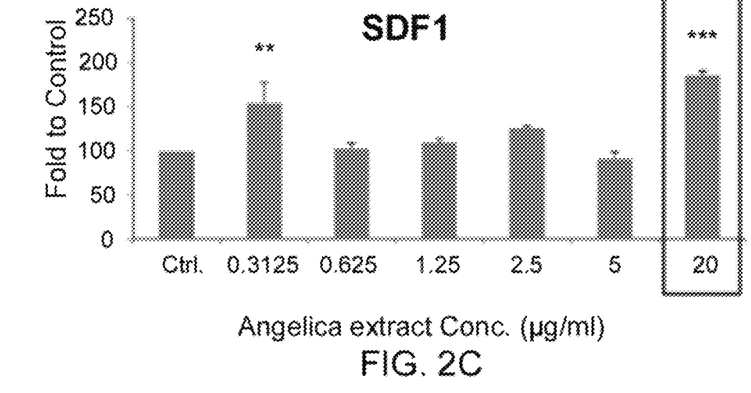
Figure 2D:
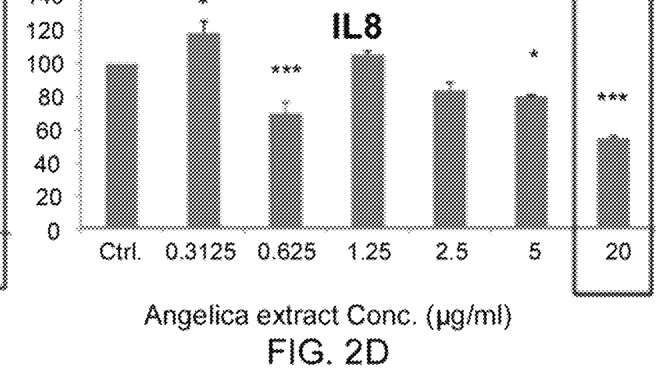

As shown in FIG. 1, after 24 hours of culture, the survival rate of the cells for treating neurodegenerative diseases was decreased when the concentration of the *angelica* extract was more than 160 µg/mL. After 48 hours of culture, the survival rate of the cells for treating neurodegenerative diseases was decreased when the concentration of the *angelica* extract was more than 80 µg/mL.

Additionally, the adipose-derived mesenchymal stem cells were cultured in 0, 0.3125, 0.625, 1.25, 2.5, 5, and 20 µg/mL *angelica* extract for 24 hours, respectively. The gene expressions of Nuclear receptor related 1 protein (Nurr1), brain derived neurotrophic factor (BDNF), stromal cell-derived factor 1 (SDF1), and Interleukin 8 (IL-8) in the cells for treating neurodegenerative diseases were analyzed by real-time PCR to determine the optimal dose in the treatment.

As shown in FIG. 2, the expression of Nurr1, BDNF, and SDF1 genes in the cells for treating neurodegenerative diseases was increased, but the expression of IL-8 gene was suppressed at 20 µg/mL of the *angelica* extract. The gene expression of BDNF in the adipose-derived mesenchymal stem cells treated with 5 µg/ml and 20 µg/mL *angelica* extract increased, which indicates that the treated adipose-derived mesenchymal stem cells secreted brain derived neurotrophic factor (BDNF). Since BDNF promotes the survival, regeneration, and differentiation of midbrain dopaminergic neurons (mDA), cells secreting BDNF can be used to treat neurodegenerative diseases. Moreover, the increased SDF1 gene expression represents an increased ability to attract endogenous stem cells to move to injured areas and to help neuron repair. The decreased IL-8 gene expression represents a reduction in the inflammatory response.

The cells were further tested for changes in mitochondrial membrane potential of adipose-derived mesenchymal stem cells with JC-1 dye. JC-1 dye is a potential-dependent dye.

JC-1 dye is characterized by the presence of green fluorescent (FL1) monomer in the in vivo mitochondrial membrane when the membrane potential is less than 100 mV. When the membrane potential gradually increases, JC-1 aggregates to form red J-aggregates (FL2) in the mitochondrial inner membrane. On the other hand, when the membrane potential decreases, JC-1 forms a green fluorescent monomer (FL1). This potential-dependent color shift can be analyzed qualitatively and quantitatively using flow cytometry. Therefore, the ratio of FL2/FL1 can be used as a criterion for determining membrane potential.

Figure 3:
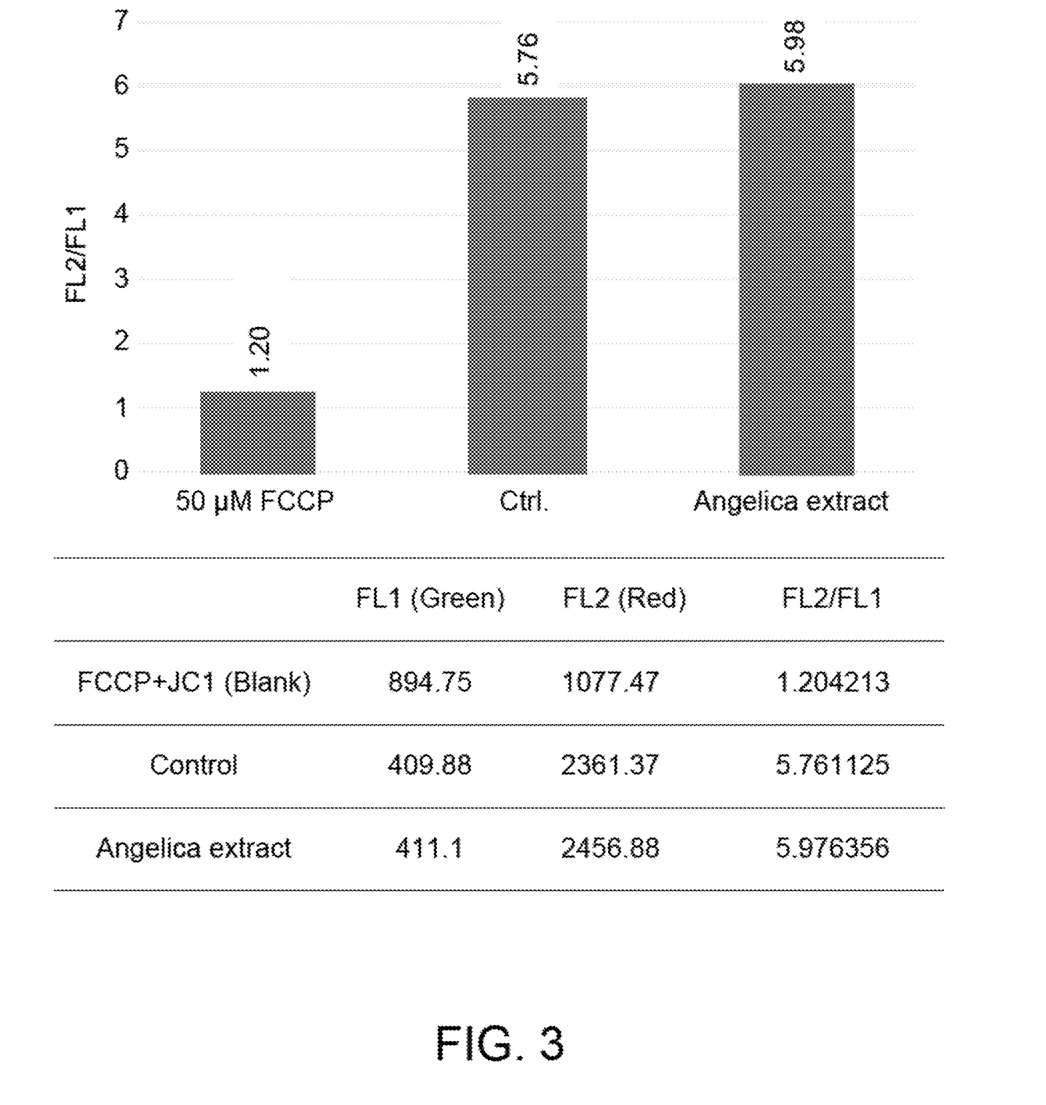
FIG. 3 illustrates the membrane potential of mitochondria of the adipose-derived mesenchymal stem cells treated with *angelica* extract detected by JC-1 dye.

As shown in FIG. 3, the red (FL2)/green (FL1) ratio (5.91) of mitochondria of the adipose-derived mesenchymal stem cells treated with *angelica* extract (ie, the cells of the present invention for treating neurodegenerative diseases) was significantly higher than the red (FL2)/green (FL1) ratio (5.76) of the untreated adipose-derived mesenchymal stem cells. This indicates that the mitochondrial membrane potential of the adipose-derived mesenchymal stem cells treated with the *angelica* extract is higher than the mitochondrial membrane potential of the untreated adipose-derived mesenchymal stem cells. That is, the adipose-derived mesenchymal stem cells treated with *angelica* extract have stronger mitochondria function than the untreated adipose-derived mesenchymal stem cells. When the stem cells begin to differentiate, the stronger mitochondria function helps to quickly switch to OXPHOS mode for differentiation.

In addition, the above-mentioned cells were analyzed by flow cytometry for the expression of surface antigen molecules CD34 (hematopoietic progenitor cell antigen), CD45 (leukocyte common antigen), CD73 (ecto-5'-nucleotidase), CD90 −1 (thymus cell antigen), and CD105 (Endoglin).

As shown in Table 1, the expression of the surface antigen molecules CD34, CD45, CD73, CD90, and CD105 of the adipose-derived mesenchymal stem cells treated with the *angelica* extract, ie. the cells for treating neurodegenerative diseases of the present invention, is identical to the expression of those surface antigen molecules of untreated adipose-derived mesenchymal stem cells, which means the two groups of cells both have a cluster of differentiation (CD) marker expression profile of $CD34^-$, $CD45^-$, $CD73^+$, $CD90^+$, and $CD105^+$. The results indicate that the cells for treating neurodegenerative diseases of the present invention still have the characteristics of stem cells.

TABLE 1

Expressions of cell surface markers of CD34, CD45, CD73, CD90, and CD105 of the adipose-derived mesenchymal stem cells treated with *angelica* extract detected by flow cytometry.

| CD marker | CD34 | CD45 | CD73 | CD90 | CD105 |
|---|---|---|---|---|---|
| Control | 0.54% | 0.21% | 99.04% | 99.08% | 97.73% |
| Cells treated with *angelica* extract | 0.37% | 0% | 99.38% | 99.17% | 98.28% |

Based on the above results, the adipose-derived mesenchymal stem cells treated with the *angelica* extract still have the characteristics of stem cells with stronger mitochondria functions. Therefore, the adipose-derived mesenchymal stem cells treated with the *angelica* extract, ie. the cells for treating neurodegenerative diseases of the present invention, can quickly differentiate into neurons after being administered to the subjects because of the characteristics of stem cells. In addition, the adipose-derived mesenchymal stem cells treated with the *angelica* extract secrete brain derived neurotrophic factor (BDNF) to increase the repair, survival, regeneration and differentiation of midbrain dopaminergic neurons (mDA). Through both mechanisms, the cells for treating neurodegenerative diseases of the present invention can be used to treat neurodegenerative diseases.

Example 2

Establishment of Induced Parkinson's Disease Mouse Model

C57BL/6 male Mice (eight weeks old), weighing 25 g, were purchased and used in this Example. After mice were divided into four groups, a few days of adaptation was provided to avoid stress and anxiety to affect the experimental process and the results of analysis. One day before the experiment, neurobehavioral observations and analysis were carried out first. Ten minutes before the surgery, 4% cholra hydrate was administered to mice at a dosage of 1 mL/g/Kg bodyweight. 0.25 mL of 4% chloral hydrate was administered to mice with a body weight of 25 g. Further, mice were anesthetized with isoflurane to prevent the mice waking up during the surgery.

1-methyl-4-phenyl-1,2,3,6-tetrahydropyridine (MPTP) dissolved in saline was used to induce Parkinson's disease in mice. The mice were administered with MPTP four times daily intraperitoneal (I.P.) injection with a 2-hours interval between injections at a dosage of 20 mg/kg. $1 \times 10^6$ cells were injected to mice in experimental groups as shown in Table 2.

(1) Group 1 (Control Group): No MPTP Injection
(2) Group 2 (Negative Control Group): MPTP Injection to Induce Parkinson's Disease+Saline
(3) Group 3 (Experimental Group): MPTP Injection to Induce Parkinson's Disease+$1 \times 10^6$ Adipose-Derived Mesenchymal Stem Cells
(4) Group 4 (Experimental Group): MPTP Injection to Induce Parkinson's Disease+$1 \times 10^6$ the Cells for Treating Neurodegenerative Diseases of the Present Invention

TABLE 2

| | | Conditions of Animal Tests | | | |
|---|---|---|---|---|---|
| | | Group 1 Control Group | Group 2 MPTP | Group 3 MPTP | Group 4 MPTP |
| Cell Therapy | Cell Type | — | Saline | Adipose-derived mesenchymal stem cells | The cells for treating neurodegenerative diseases of the present invention |
| | Pre-treatment of Cells | — | — | — | *Angelica* extract |
| Mice number | | 3 | 3 | 3 | 3 |

Example 3

Neurobehavioral Analysis After/Before Surgery 3.1 Beam Walking Analysis

Beam walking test was used to analyze the balance ability of mice. Mice were placed at the extremity of an 80 cm-long wooden narrow beam and record the time spent in walking and the number of foot slips to analyze the balance and coordination of mice. Test time was 60 seconds. If the mice could not traverse the entire beam successfully within 60 seconds, the spent time was recorded as 60 seconds.

Figure 4A:
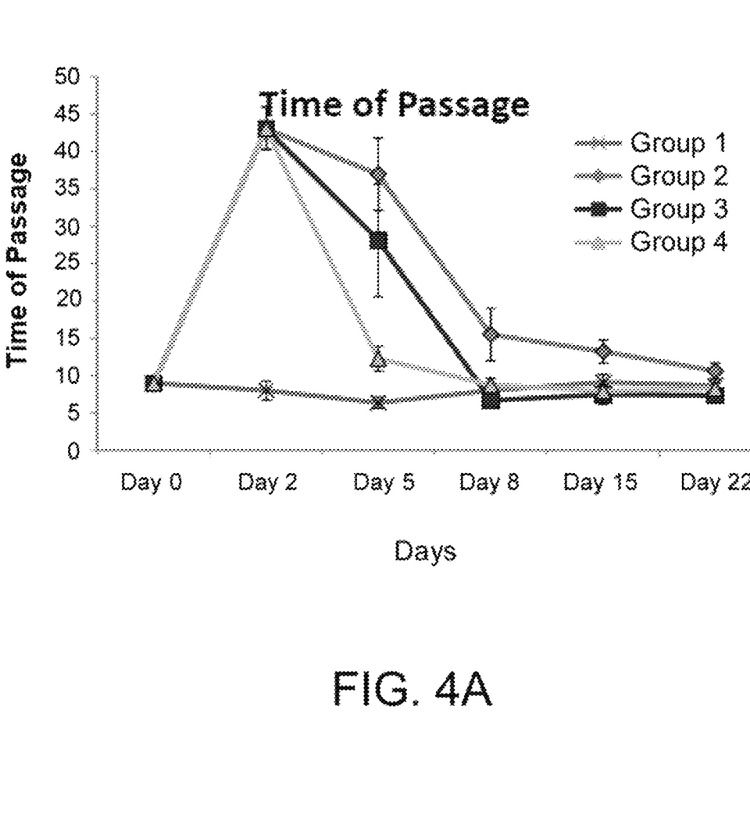
FIGS. 4A-4D illustrate the results of Beam walking test. The results show that after the mice were administrated with adipose-derived mesenchymal stem cells (Group 3) or the cell for treating neurodegenerative diseases of the present invention (Group 4), the activities on balance control of the mice was significantly improved, and the activities on balance control in Group 4 was better than Group 3.
Figure 4B:
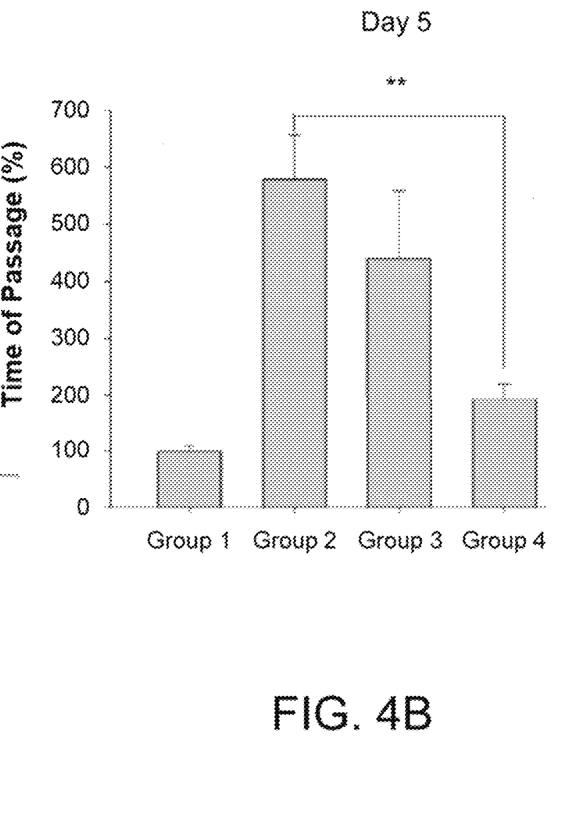

As shown in FIG. 4A and FIG. 4B, MPTP-induced Parkinson's disease model mice (Group 2) could not complete the beam walking test. After injection of adipose-derived mesenchymal stem cells (Groups 3) or the cells for treating neurodegenerative diseases (Groups 4), the balance abilities of mice were significantly improved.

Figure 4C:
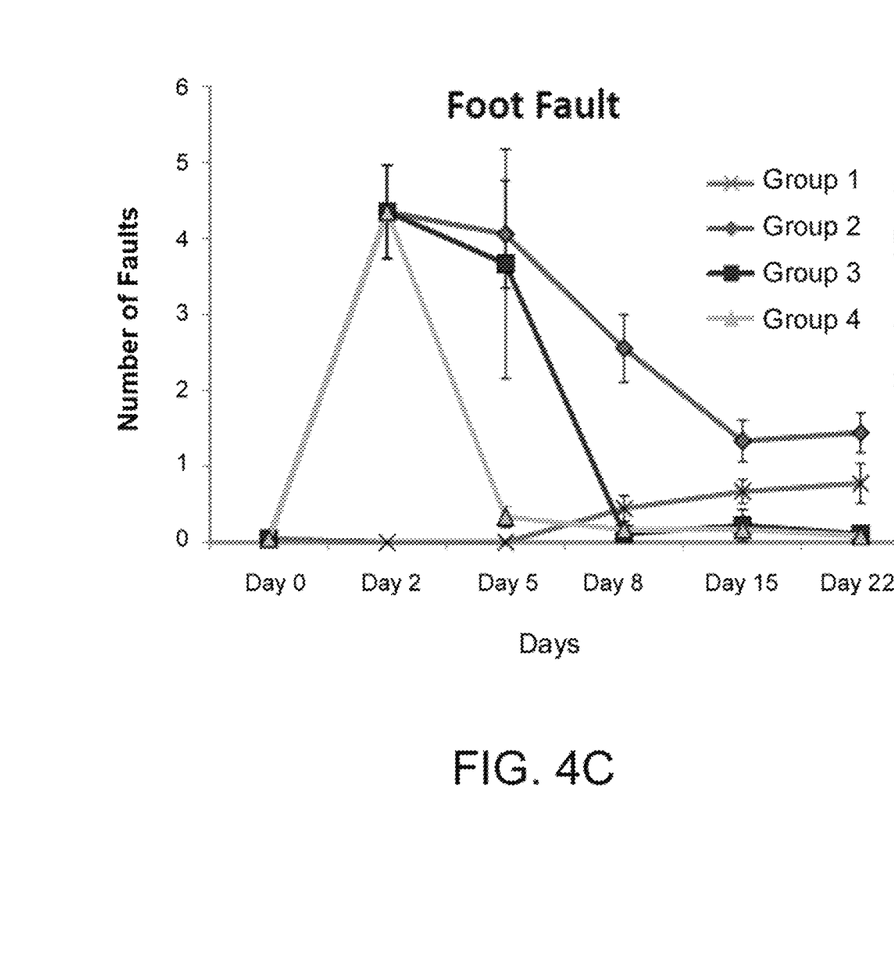
Figure 4D:
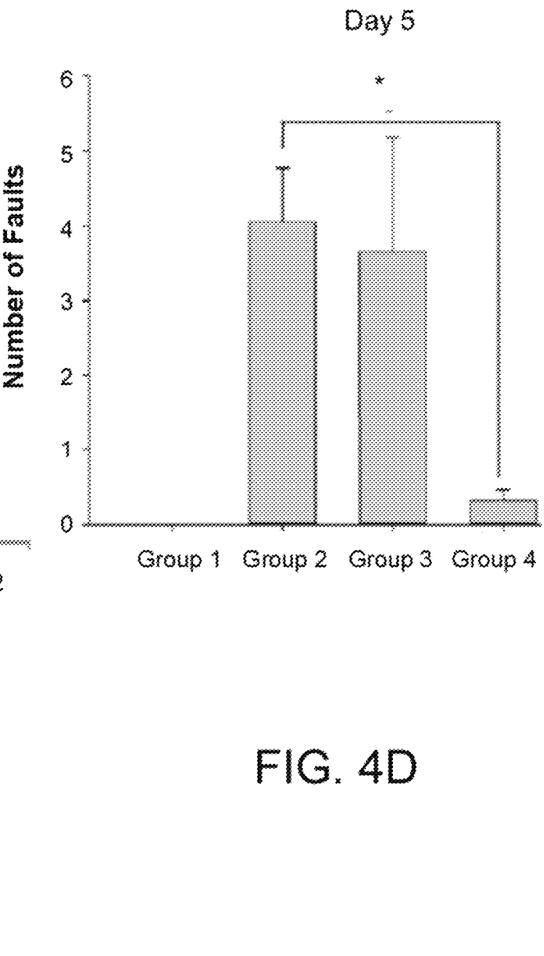

As shown in FIG. 4C and FIG. 4D, the number of foot slips was increased in mice after administration of MPTP (Group 2). After rejection of adipose-derived mesenchymal stem cells (Groups 3) or the cells for treating neurodegenerative diseases (Groups 4), the number of foot slips was decreased.

The results indicated that the cells for treating neurodegenerative diseases (Group 4) had a better treatment effect in mice compared to adipose-derived mesenchymal stem cells (Group 3).

3.2 Rotarod Analysis

Rotarod analysis was used to determine the balance and coordination abilities of mice. One week before the experiment, the mice were trained to perform on the rotarod at 3 minutes. After surgery, the recovery of balance in mice was analyzed by rotarod analysis at 5 rpm.

Figure 5A:
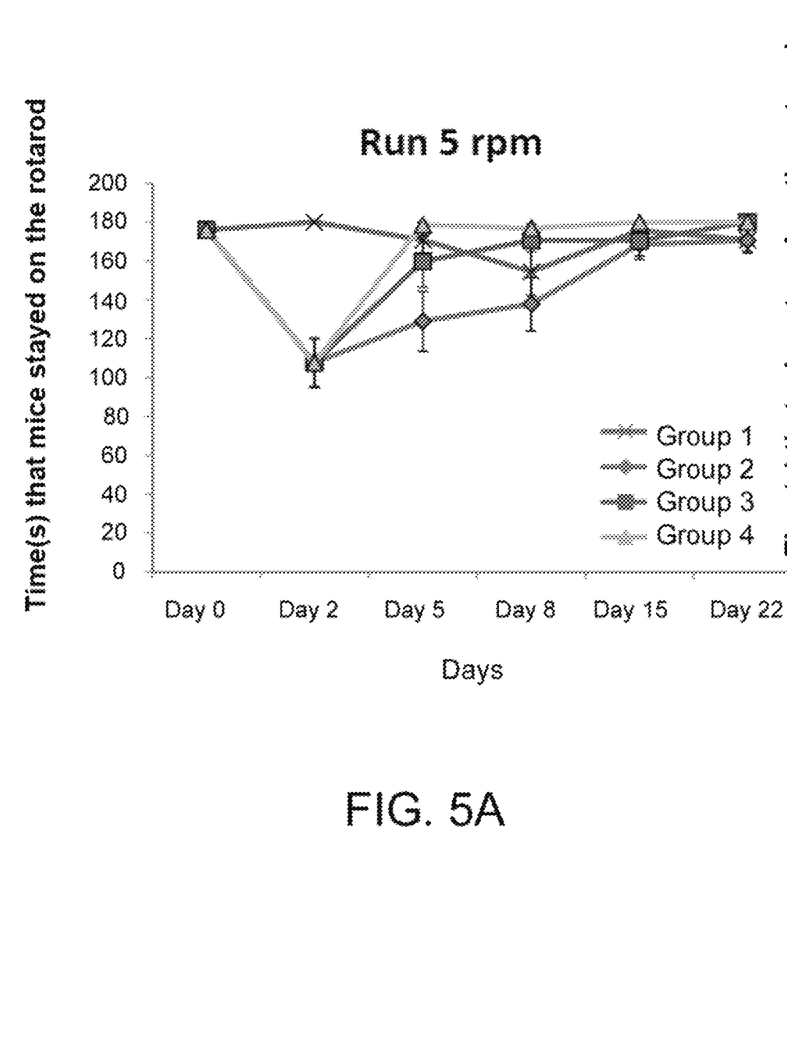
FIGS. 5A and 5B illustrates the results of rotarod test. The results indicated that after the mice were administrated with adipose-derived mesenchymal stem cells (Group 3) or the cell for treating neurodegenerative diseases of the present invention (Group 4), the coordination and balance of mice were recovered, and the recovery in Group 4 was better than Group 3.
Figure 5B:
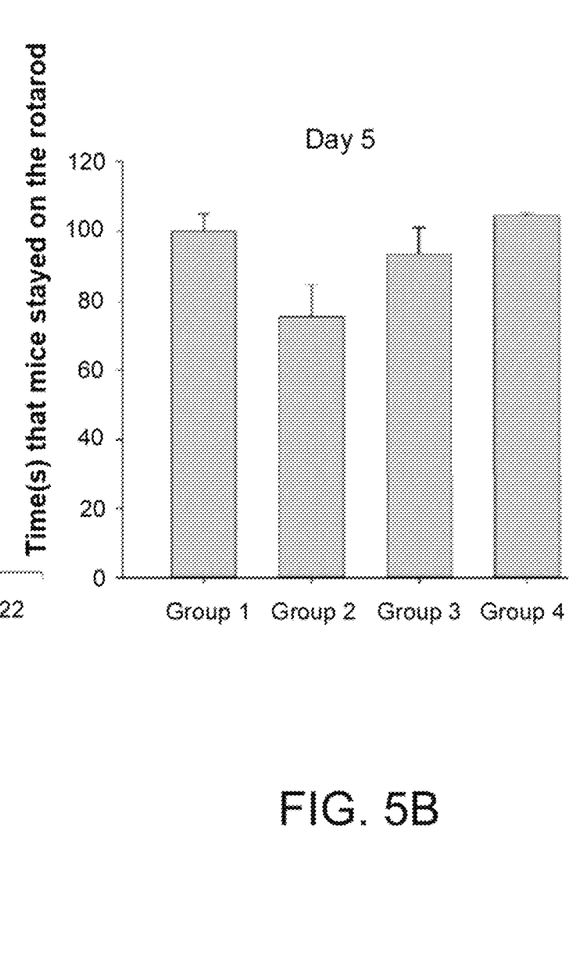
Figure 6A:
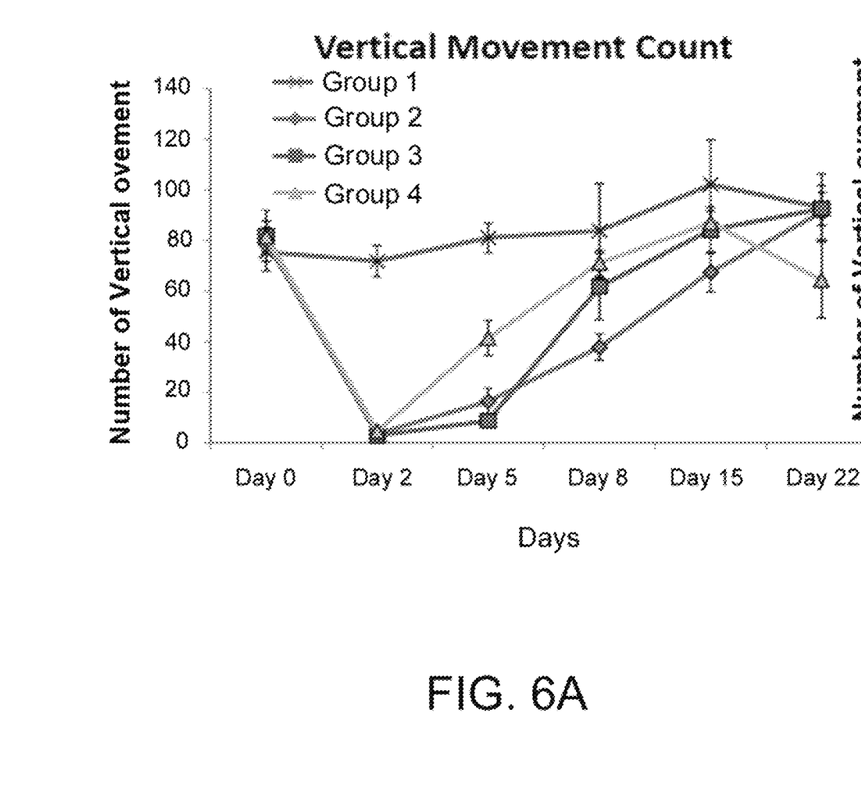
FIGS. 6A-6F illustrate the results of locomotor activity box test. The results indicated that after the mice were administrated with adipose-derived mesenchymal stem cells (Group 3) or the cell for treating neurodegenerative diseases of the present invention (Group 4), the behavior ability of mice was recovered, and the recovery in Group 4 was better than Group 3.
Figure 6B:
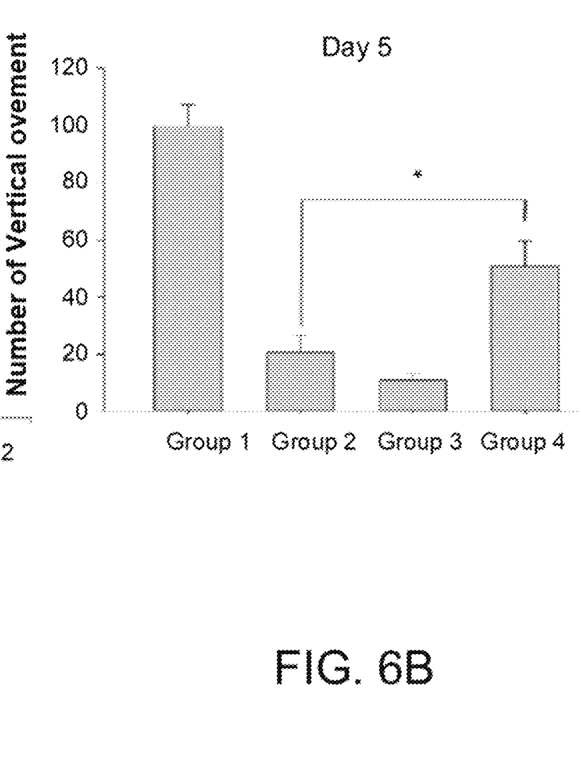
Figure 6C:
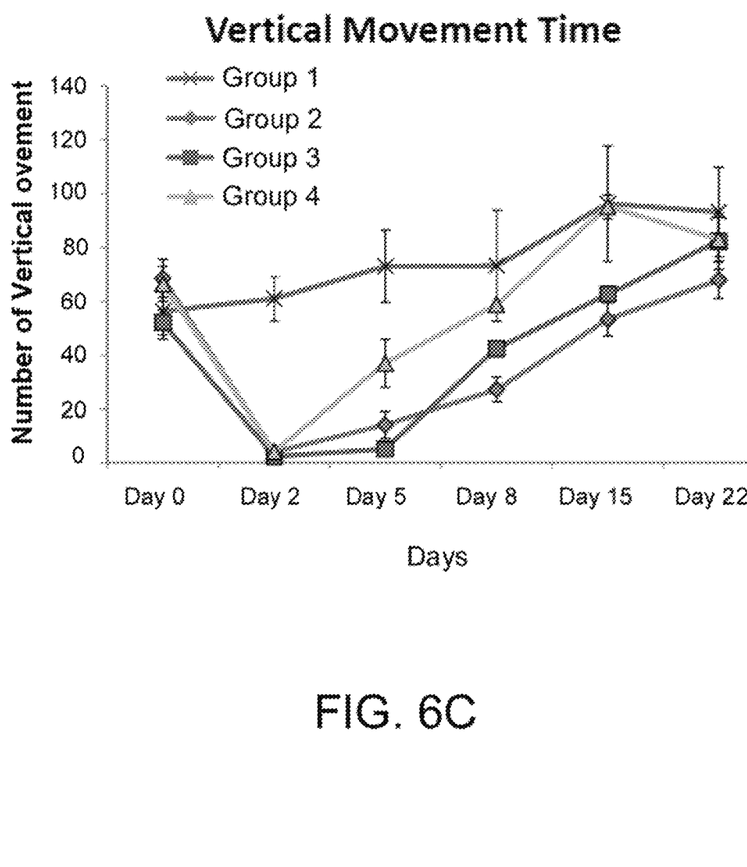
Figure 6D:
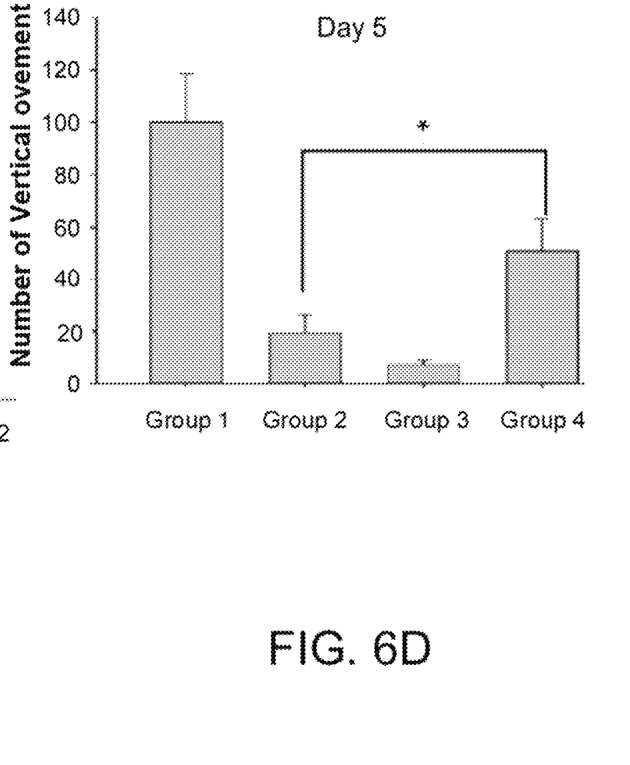
Figure 6E:
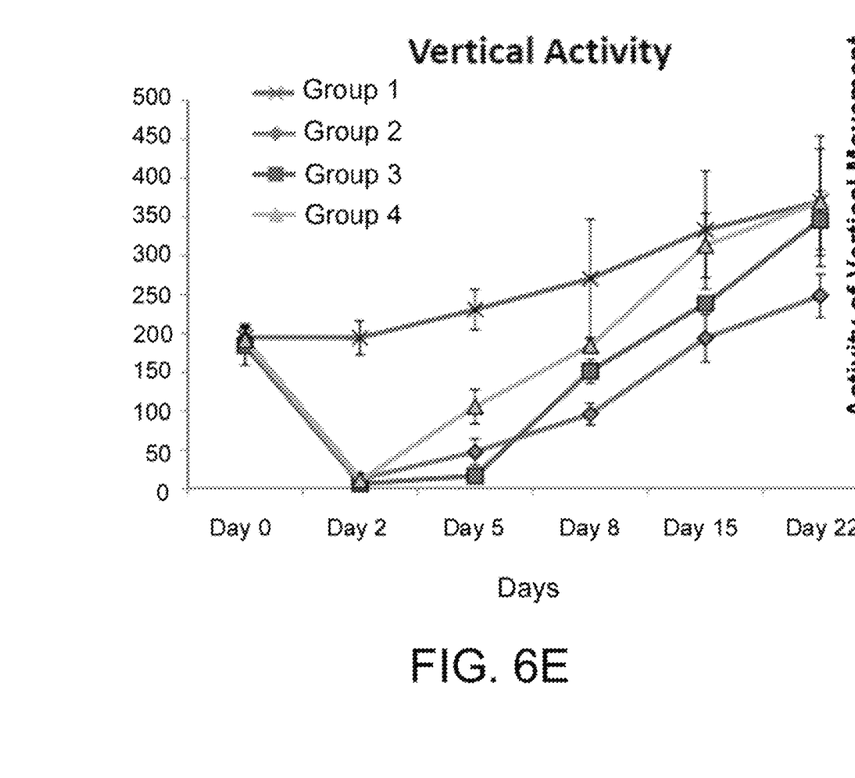
Figure 6F:
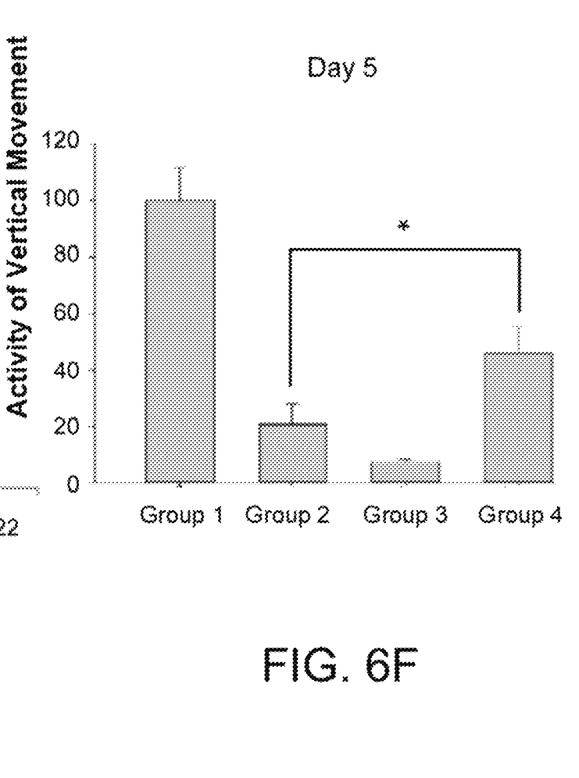

As shown in FIG. 5A and FIG. 5B, the balance and coordination abilities in mice were significantly decreased after administration of MPTP (Group 2). However, after injection of adipose-derived mesenchymal stem cells (Groups 3) or the cells for treating neurodegenerative diseases (Groups 4), the balance and coordination abilities in mice were recovered, preferably injection of the cells for treating neurodegenerative diseases of the present invention (Group 4).

3.3 Locomotor Activity Box

Before the monitor, mice were placed in the chamber for 10 to 20 minutes to adapt the environment. The locomotor activity box was connected to a computer to monitor and record the mouse locomotor activities including running (horizontal locomotion), head rising/climbing, and total distance traveled for 30 minutes. The data were collected for statistical analysis As shown in FIGS. 6A-6F, the balance and coordination abilities were decreased in mice after administration of MPTP (Group 2). However, after injection of adipose-derived mesenchymal stem cells (Group 3) or the cells for treating neurodegenerative diseases (Groups 4), the number of vertical movement (FIGS. 6A and 6B), time (FIGS. 6C and 6D) and activities (FIGS. 6E and 6F), preferably injection of the cells for treating neurodegenerative diseases of the present invention (Group 4).

3.4 Analyses of Brain Damages

Mice were sacrificed with an excess dose of anesthetic (2-3 times the anesthetic dose). When mice were deeply anesthetized, mice were perfused with saline to wash out the blood and then with paraformaldehyde until all limbs became stiff to remove the brain of mice.

The skins behind ears were cut with the straight sharp scissor and the skin over the skull was vertically cut to expose the skull. The upper parts of the neck were cut by scissors to separate the neck bones and cerebellum and then the skulls were cut through the nose without cutting the brain, carefully. The parts below the brain were cleaned to remove the brain. The brain was dehydrated and placed on an operation table. The operation table was pre-cooled to prevent brain damages.

The cerebellum and olfactory bulb in brain were removed and the right and left sides of the brain were cut into two parts. The parts were embedded in optimal cutting temperature compound (OTC) and cryosectioned.

Figure 7:
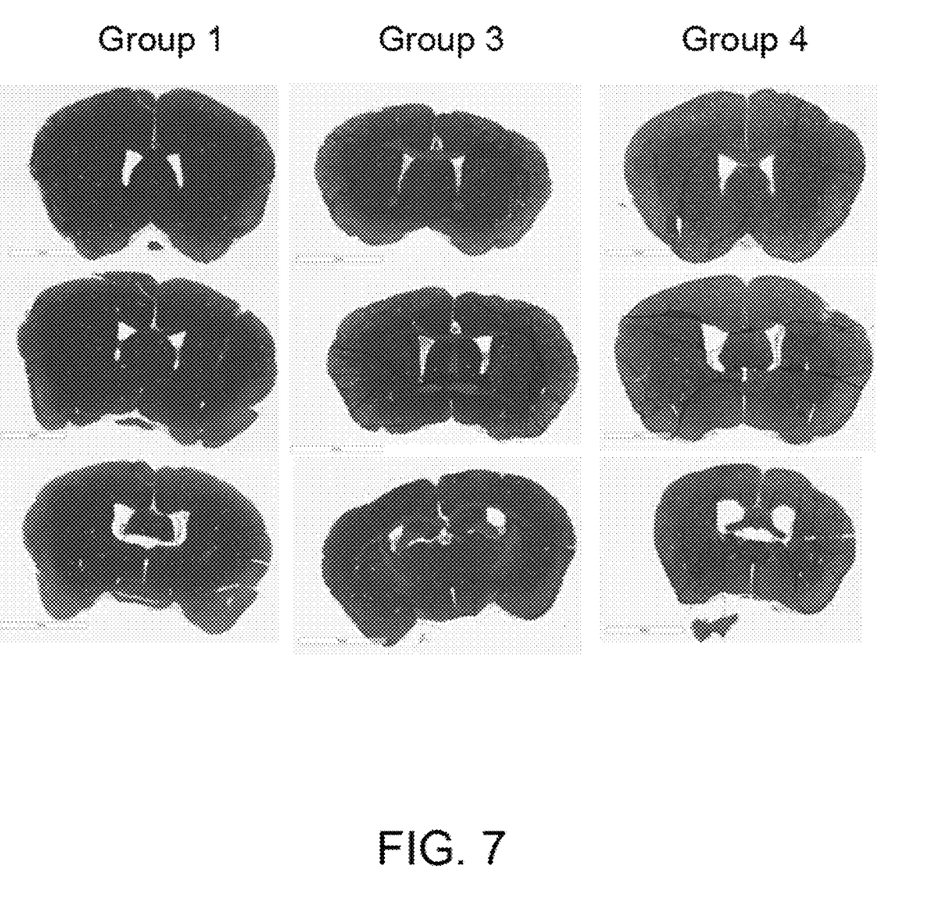
FIG. 7 illustrates the results of brain sections stained by H&E (Hematoxylin and Eosin). The results indicated that adipose-derived mesenchymal stem cells and the cell for treating neurodegenerative diseases of the present invention did not have toxicity to neurons and would not enhance the inflammation in brain after injection.

The brain sections stained by H&E were analyzed to determine the damages of inflammation response in brain cells of mice in Groups 3 and 4. The results indicated that no damage or inflammation response was found in brain cells of mice in Groups 3 and 4 (FIG. 7).

3.5 Analyses of Cell Differentiation into Dopaminergic Neurons

Figure 8A:
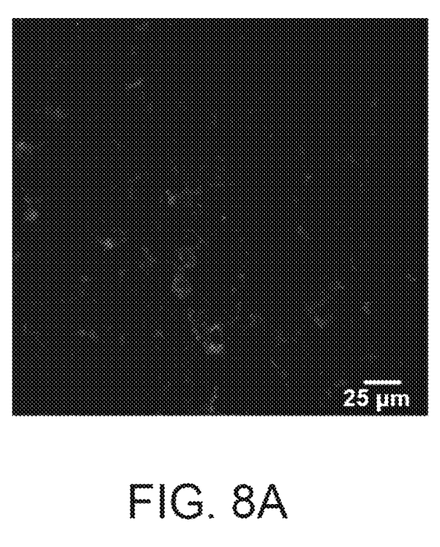
FIGS. 8A-8D illustrate the results of immunocytochemistry of brain cells of mice of Group 1 (control group, FIG. 8A), Group 2 (MPTP+Saline, FIG. 8B), Group 3 (MPTP+adipose-derived mesenchymal stem cells, FIG. 8C), and Group 4 (MPTP+the cells for treating neurodegenerative diseases of the present invention, FIG. 8D). Arrows indicates that the cells for treating neurodegenerative diseases of the present invention differentiated into dopaminergic neurons in the mouse's brain (Groups 4, FIG. 8D).
Figure 8B:
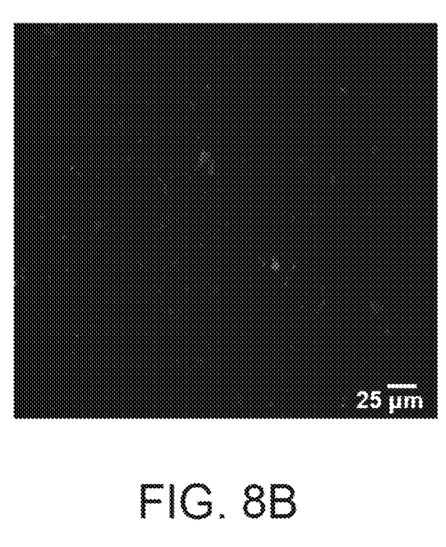
Figure 8C:
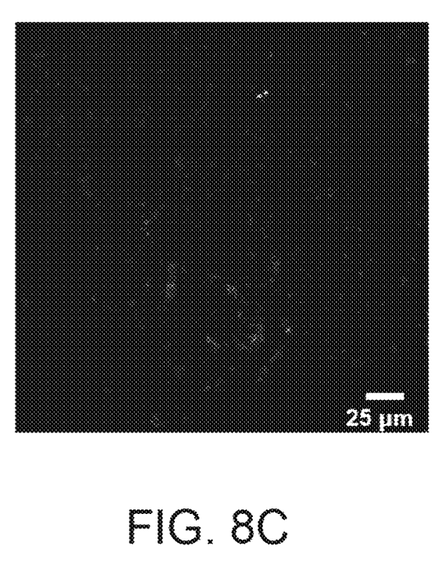
Figure 8D:
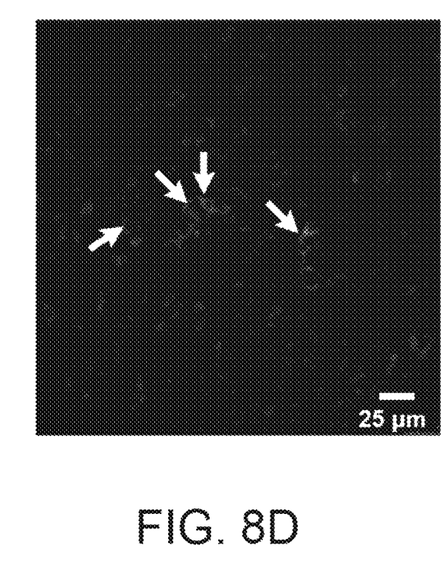

Three mice from each group was sacrificed on the fifth day after establishment of induced Parkinson's Disease mouse model to analyze whether the injected cells differentiated into dopaminergic neurons in the mice's brains. The mice's brains were fixed with 4% of paraformaldehyde by transcardial perfusion. Cryosectioning samples of the fixed brains were then analyzed by immunocytochemistry with rabbit anti-mouse tyrosine hydroxylase (TH) antibody (specifically detects dopaminergic neurons, red fluorescence), rabbit anti-human mitochondria (hMito) antibody (specifically detects human mitochondria, which indicate the injected adipose-derived mesenchymal stem cells (Groups 3) or the injected cells for treating neurodegenerative diseases of the present invention (Groups 4), green fluorescence), and DAPI (detects cell nuclei, blue fluorescence). Fluorescence images were captured using a confocal laser-scanning microscope (Fluoview 1000, Olympus), and the results were shown in FIG. 8A (Group 1), FIG. 8B (Group 2), FIG. 8C (Group 3), and FIG. 8D (Group 4). The results show that only the injected cells for treating neurodegenerative diseases of the present invention (Groups 4, FIG. 8D) have both tyrosine hydroxylase (TH) (red fluorescence) and human mitochondria (hMito) (green fluorescence) in the same cells (as indicated by the arrows in FIG. 8D, yellow fluorescence, which is the outcome of red fluorescence mixed with green fluorescence). This result indicates that the cells for treating neurodegenerative diseases of the present invention (Groups 4, FIG. 8D) differentiated into dopaminergic neurons in the mouse's brain. Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. An isolated adipose-derived mesenchymal stem cell cultured in medium with a 5~20 µg/ml *angelica* extract for 24 to 48 hours, wherein the *angelica* extract comprises butylidenephthalide or is butylidenephthalide; wherein the cell is $CD34^-$, $CD45^-$, $CD73^+$, $CD90^+$ and $CD105^+$, expresses a statistically significantly increased amount of BDNF and SDF1, has a statistically significantly increased mitochondrial membrane potential, and expresses a statistically significantly decreased amount of IL-8 as compared to untreated adipose-derived mesenchymal stem cells; wherein the cell is capable of differentiating into a dopaminergic neuron in a subject's brain; and wherein the increased mitochondrial membrane potential is determined by an increase in a ratio of red J-aggregates of JC-1 to green fluorescent monomer of JC-1 dye on mitochondrial membrane of the cell.

2. The cell for treating neurodegenerative diseases according to claim 1, wherein the *angelica* extract is butylidenephthalide.

3. A pharmaceutical composition, comprising cells according to claim 1 and a pharmaceutically acceptable salt.

4. The pharmaceutical composition according to claim 3, wherein the cells are present in an amount of 70%~99% (w/w) of the composition.

5. The pharmaceutical composition according to claim 3, wherein the cells are present in an amount of 80%~99% (w/w) of the composition.

6. A method for treating Parkinson's disease in a subject, comprising administrating a therapeutically effective number of cells according claim 1 to the subject, wherein the cells are capable of differentiating into dopaminergic neurons and thereby improving balance and coordination abilities of the subject.

7. The method according to claim 6, wherein the therapeutically effective number of cells for treating Parkinson's disease is $1\times10^4$ to $1\times10^6$ cells per mouse.

8. The method according to claim 6, wherein the therapeutically effective number of cells for treating Parkinson's disease is $3\times10^7$ to $3\times10^9$ cells per human being.

9. The method according to claim 6, wherein the cells for treating Parkinson's disease are injected into the brain of the subject.

10. A method for producing a cell according claim 1, comprising:

i) providing an isolated adipose-derived mesenchymal stem cell;

ii) culturing the isolated adipose-derived mesenchymal stem cell in medium with a 5~20 µg/ml *angelica* extract for 24 to 48 hours; wherein the *angelica* extract comprises butylidenephthalide or is butylidenephthalide; and iii) detecting, measuring, and isolating the cell that is CD34−, CD45−, CD73+, CD90+ and CD105+, expresses a statistically significantly increased amount of BDNF and SDF1, has a statistically significantly increased mitochondrial membrane potential, and expresses a statistically significantly decreased amount of IL-8 as compared to untreated adipose-derived mesenchymal stem cells; wherein the cell is capable of differentiating into a dopaminergic neuron in a subject's brain; and wherein the increased mitochondrial membrane potential is determined by an increase in a ratio of red J-aggregates of JC-1 to green fluorescent monomer of JC-1 dye on mitochondrial membrane of the cell.

* * * * *